(12) United States Patent
Langevin

(10) Patent No.: US 6,402,735 B1
(45) Date of Patent: Jun. 11, 2002

(54) MEDICAL TUBE COLLAR

(75) Inventor: Paul B. Langevin, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/443,823

(22) Filed: Nov. 19, 1999

(51) Int. Cl.$^7$ ............................................. A61M 25/00
(52) U.S. Cl. ........................ 604/523; 604/265; 604/286
(58) Field of Search ........................... 604/890.1, 891.1, 604/502, 58, 103.01, 103.02, 191, 268, 264, 265, 266, 269, 523, 285, 286

(56) References Cited

U.S. PATENT DOCUMENTS

| | | |
|---|---|---|
| 4,717,385 A | 1/1988 | Cameron et al. |
| 5,279,551 A | 1/1994 | James |
| 5,279,594 A | 1/1994 | Jackson |
| 5,389,074 A | 2/1995 | Parker et al. |
| 5,417,671 A | 5/1995 | Jackson |
| 5,647,860 A * | 7/1997 | Roth et al. .................. 604/264 |

OTHER PUBLICATIONS

Valenzuela, Roberto C. et al. (1999) "Topical Lidocaine–Prilocaine Cream (EMLA) for Thoracostomy Tube Removal" *Anesth Analg* 88:1107–1108.

* cited by examiner

*Primary Examiner*—Brian L. Casler
*Assistant Examiner*—Mark Han
(74) *Attorney, Agent, or Firm*—Saliwanchik, Lloyd & Saliwanchik

(57) ABSTRACT

The present invention pertains to a device and a method for use with medical and surgical tubing and is designed to effectively reduce the discomfort associated with the use or removal of a tube from a patient's body. The device is designed to fit around a chest tube or other medical tube so that a medication, such as ah anesthetic, can be instilled at the site the tube enters the patient's body. In one embodiment, the tube collar is cylindrical in shape having a cylinder wall defining an inner surface and an outer surface, such that the outer surface contacts the body tissue when the tube and collar are in place. The medication can be delivered to the tissue in contact with the collar through channels imbedded within the cylinder wall that have openings to the outer surface or via channels that are present on the outer surface of the cylinder wall.

18 Claims, 3 Drawing Sheets

MEDICAL TUBE COLLAR

FIELD OF INVENTION

This invention relates generally to surgical devices, and more specifically, to a device fitted about a catheter tube inserted into a patient through an opening in the patient's body to provide a local anesthetic agent to the tissue around the opening.

BACKGROUND OF THE INVENTION

Catheters have been used for many years to remove body fluids, whereby a sharp pointed instrument is fitted with a cannula and is used to insert the cannula into a body cavity as a drainage outlet. The common practice is to place a tube into a body cavity of a patient and then to initiate drainage of body build using gravity or a vacuum source. Once the accumulation of fluid in the body cavity has been relieved, the catheter is removed from the patient. The removal of the catheter from the patient's body can cause severe pain and discomfort to the patient.

A variety of devices and methods have been introduced to try to alleviate some of the patient's discomfort during medical procedures involving the use of catheters and tubes in the body. For example, Valenzuela et al. (1999) describe the topical application of an anesthetic (lidocaine-prilocaine cream) prior to postoperative thoracostomy tube removal to reduce pain during the procedure.

U.S. Pat. No. 5,389,074 to Parker discloses an endotracheal tube and a nasogastric tube for oral or nasal insertion into a patient's trachea and pharynx, respectively, to clear a pathway to the lungs or stomach. The tube is surrounded by a jacket through which an anesthetic can be provided to prevent gagging or coughing of the patient during the procedure and the subsequent removal of the tube. U.S. Pat. Nos. 5,279,594 and 5,417,671 to Jackson disclose an intubation device for introduction into body passages that has topical anesthetic properties incorporated into the polymeric material making up the walls of the device. When the tube is inserted within the body passage the anesthetic compound diffuses to the surface of the body tissue in contact with the tube. The anesthetic alleviates the discomfort experienced by the patient and suppresses the ejection reaction, such a gagging or coughing of the patient.

U.S. Pat. No. 5,279,551 to James discloses a Trocar catheter which is capable of administering pain relief at localized points. As disclosed, during the vacuum process the patient can feel some discomfort. The cited invention is capable of simultaneous removing the fluids and dispensing localized medication at the point of vacuum to alleviate such discomfort.

U.S. Pat. No. 4,717,385 to Cameron et al. discloses a device for anchoring a tube, such as a gastrostomy tube, that has been inserted into a patient's body to minimize tube movement and prevent unwanted removal of the tube from the body.

While the cited examples are capable of providing anesthetic to a localized point, none are directed to providing anesthetic at an opening, such as a surgical incision, to alleviate the patient's discomfort during removal of a tube or other device through the opening. As can be understood from the above, there remains a need in the art for a means to alleviate a patient's discomfort during removal of a medical tube or other device from an opening, incision or ostomy site.

BRIEF SUMMARY OF THE INVENTION

The present invention concerns a device for use with medical and surgical tubing and is designed to effectively reduce the discomfort associated with the presence or removal of a tube from a patient's body. The device is designed to fit around a medical tube or device, such as a chest tube, so that an anesthetic or other medication can be instilled at the site the tube enters the patient's body. In one embodiment, the tube collar is substantially cylindrical in shape having a cylinder wall defining an inner surface and an outer surface, such that the outer surface contacts the patient's body tissue when the tube and collar are in place. The anesthetic can be delivered to the tissue in contact with the collar through channels imbedded within the cylinder wall that have openings to the outer surface or via channels that are present on the outer surface of the collar that are in contact with the tissues surrounding the wall of the tube. Alternatively, the tube collar can comprise a membrane which is porous and capable of allowing anesthetic or medication to pass through to the tissue surrounding the collar.

During use, medical tubing is inserted into an entry site or opening in a patient's body. A tube collar of the present invention is then attached to the medical tube in a manner such that the inner surface of the tube collar wraps around the outer surface of the medical tube. The length of the tube is adjusted as necessary to treat the patient before the collar is secured to the tube so that medication can be delivered to the site of interest regardless of where that location is relative to the length of the tube. Once fluids have been drained, the tube is ready for removal from the patient's body. Prior to and/or during the removal of the tube, an anesthetic and/or other medication is injected into the collar, wherein the anesthetic travels though the channels in the tube collar and is released at the surface of the tube collar. The anesthetic is absorbed from the collar into the body tissue, thereby locally anesthetizing the body tissue at the entry site. Once the medication has provided the desired level of anesthesia, the tube can be removed from the patient's body.

DETAILED DISCLOSURE OF THE INVENTION

Figure 1:
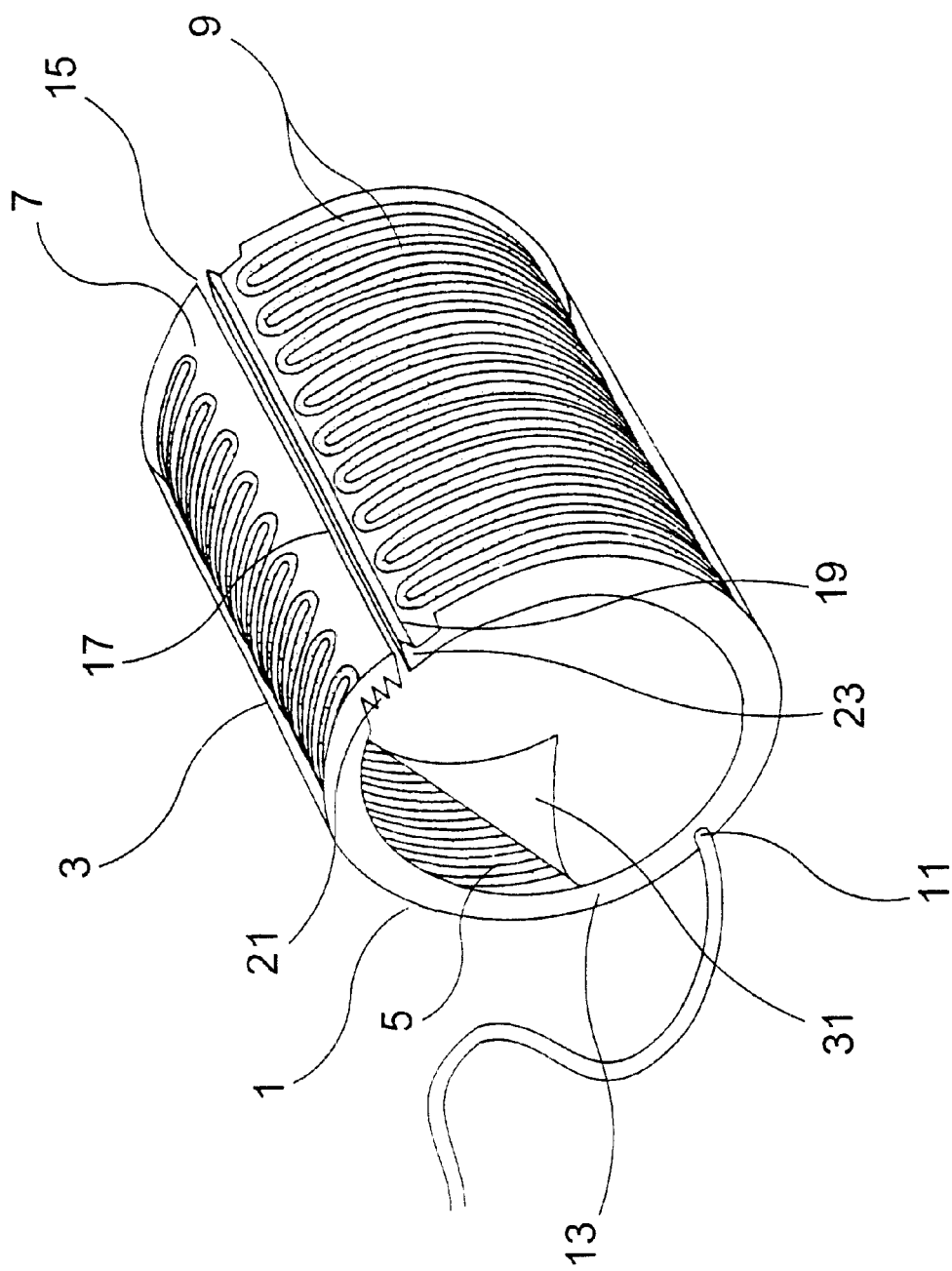
FIG. 1 shows one embodiment of a tube collar of the present invention.

The subject invention concerns devices and methods for delivery of medications or drugs for reducing discomfort associated with the use and/or removal of tubes and other devices from a patient's body. One embodiment of a tube collar of the present invention is depicted in FIG. 1. The tube collar 1 is substantially cylindrical in shape having a cylinder wall 3 defining an inner surface 5 and an outer surface 7. The outer surface is in physical contact with the body tissue when the tube collar is in use. Channels or ducts 9 are imbedded within the cylinder wall. The channels or ducts are perforated or otherwise have openings to the outer surface of the cylinder through which a medication that is delivered to the collar can pass for delivery to tissue in contact with the outer surface 7 of the cylinder wall 3. The surface covering the channels can also be constructed to provide for permeability of the medications across the surface covering and into the tissue. Preferably, a medication delivery port 11 for delivery of drugs, such as anesthetics or antibiotics, which is connected to the channels 9 is located at an end 13 of the cylinder wall of the tube.

The medications which can be delivered by the tube collar include but are not limited to antibiotics and anesthetics. In a preferred embodiment, the medication is an anesthetic. The use and delivery of combinations of different medications as required for treatment of the patient is contemplated by the present invention.

Figure 2:
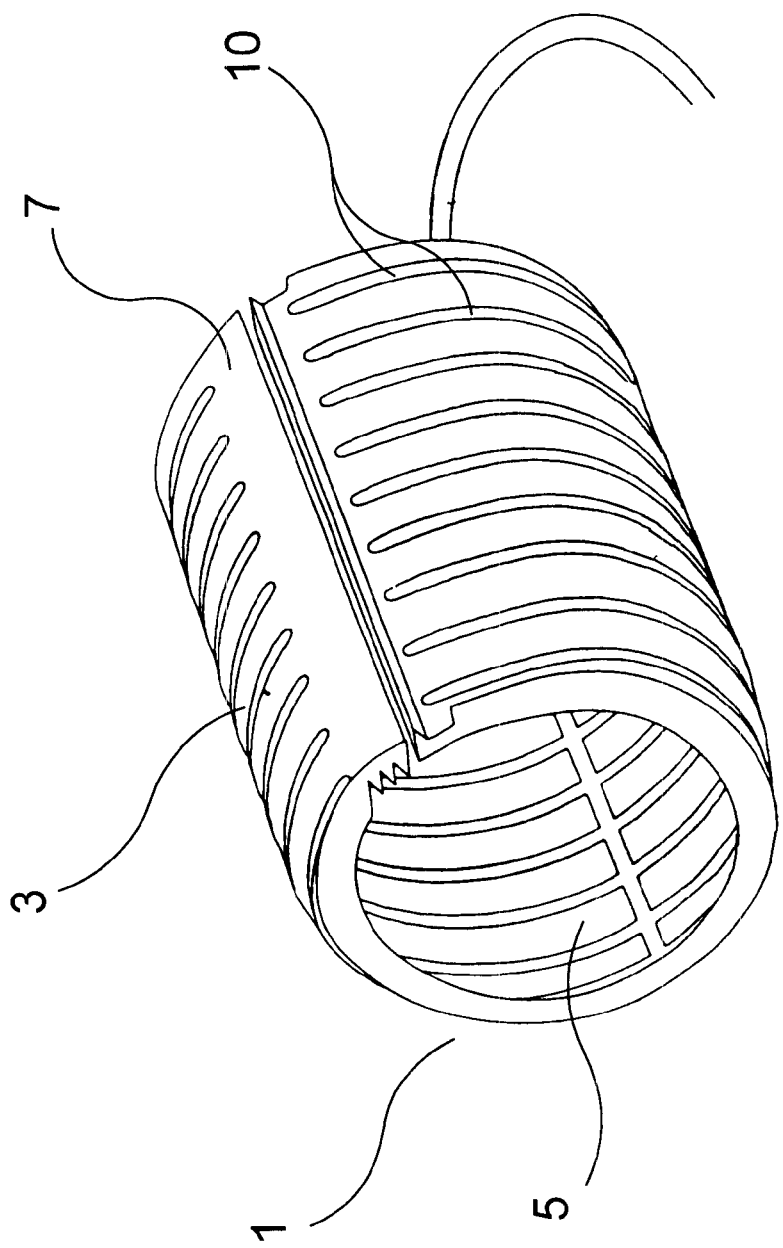
FIG. 2 shows another embodiment of a tube collar of the present invention.

Another embodiment of the present invention is depicted in FIG. 2. In this embodiment, the tube collar is similar to the collar depicted in FIG. 1 except that the outer surface of the collar comprises a series of open channels 10. While in close contact with the patient's body tissue, medication is delivered to the tube collar and allowed to flow in the channels 10 for release to the surrounding tissue.

In one embodiment of the present invention, illustrated in FIG. 1, the tube collar is configured such that a slit 15 having a first edge 17 and second edge 19 runs the axial length of the tube collar. This configuration permits the diameter of the tube collar to be adjusted, to allow the subject tube collar to be placed on and fit around a variety of tubes having different size diameters. In a preferred embodiment, the slit comprises a locking mechanism. Preferably, one edge of the slit comprises a plurality of substantially rigid acutely angled teeth 21 molded into the inner surface of the cylinder wall. The opposite edge of the slit comprises a tongue 23, which substantially mates with the teeth. The tube collar can be locked about a chest tube by compressing the collar such that the tongue 23 engages the teeth 21 to substantially lock the first and second edge together. The tube collar is compressed until securely fitted about the tube.

The inner surface of the tube collar can be coated with an adhesive for securing the collar to a tube. With the adhesive backing the tube collar can be securely affixed about a tube, thereby preventing slippage of the tube collar along the tube during the removal of the tube from the patient. Preferably, the adhesive backing is protected by a sterile, removable covering 31, which can be peeled off prior to attachment of the collar to the tubing (FIG. 1). The tube collar device can also be attached to a tube via surface fittings adapted for attaching the collar to the tube.

Figure 3:
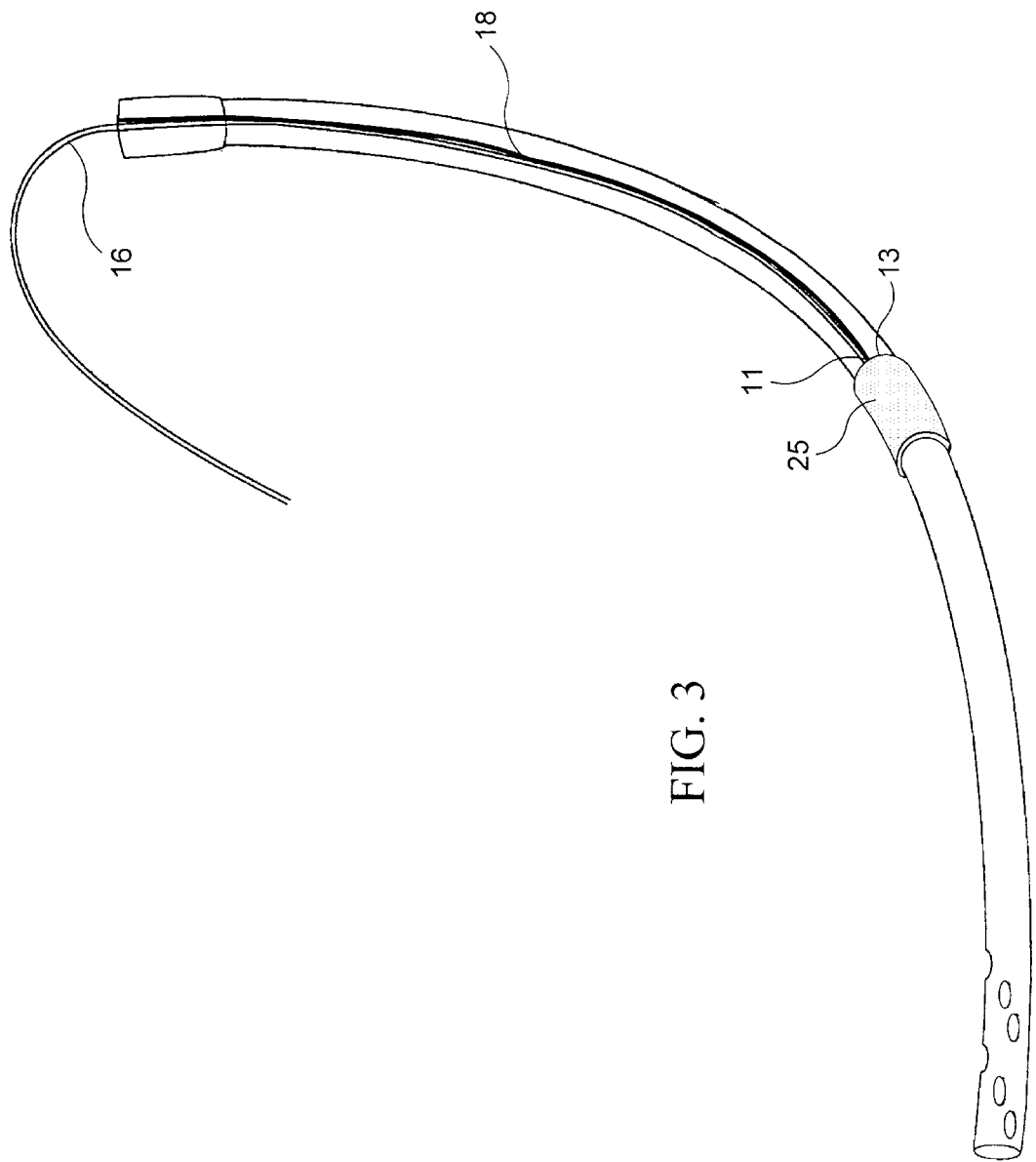
FIG. 3 shows a tube collar of the present invention attached to a medical tube.

When in use, the tube collar is fitted about a medical tube (FIG. 3). The tube is inserted into an entry site or opening in a patient's body such that the tube collar is positioned within the entry site. The inner surface of the tube collar is secured around the medical tube at the required location, such that the outer surface of the collar is in physical contact with the body tissue surrounding the entry site. Prior to the removal of the tube, a medication such as an anesthetic can be delivered to the tube collar device. In one embodiment, medication is delivered to the tube collar by way of a medication delivery port 11 at an end 13 of a cylinder wall of the tube collar. The medication port is connected to and provides fluid communication with the channels. A medication delivery tube 16 or device can be attached to the medication port. The tube or device to which the collar is attached can have a groove 18 into which the medication delivery tube 16 and port 11 can detachably fit. The anesthetic can be delivered to the tissue in contact with tube collar through channels 9 imbedded within the cylinder wall that have openings to the outer surface (FIG. 1), via channels 10 that are present on the outer surface of the collar (FIG. 2), or via a porous membrane 25 (FIG. 3), thereby providing a local anesthetic effect on the body tissue at the entry site or opening of the patient's body. Once the medication has been delivered to the body tissue at the opening or entry site and a sufficient amount of time allowed to elapse to provide an acceptable level of anesthetic effect, the medical tube can be removed from the patient's body.

The tube collar of the present invention can be made of any suitable material including rubber or plastic materials such as, for example, polyvinyl chloride, polyethylene or "TEFLON." Preferably, the material used to construct the tube collar is composed of an inert, non-toxic material that is suitable for use in medical devices used on humans.

Tube collar shapes other than cylindrical for use with openings and tubes of different shapes are contemplated within the scope of the present invention. For example, a collar of the present invention can be constructed in an oval shape to fit a tube and/or body opening that is oval in cross-section. In addition, the tube collar of the present invention can be produced in any axial length that is appropriate for the thickness of the tissue or opening where the tube is to be inserted.

Anesthetics that can be used with the present invention include lidocaine, prilocaine, dibucaine, and the like. Suitable anesthetics and dosages can be selected and formulated by the ordinarily skilled clinician for delivery to wound tissue using the tube collar of the present invention.

The subject invention also concerns methods for delivering medications such as anesthetics to a wound site or opening in a patient's body where a medical tube or other device is to be inserted and later removed. In one embodiment, a tube collar of the present invention is attached to the outside of the tube inserted in the patient's body and the tube collar positioned so that the outer wall of the collar is in contact with body tissue at the opening or wound site. Medication can then be delivered to the tube collar which releases the medication to the surrounding tissue. In a preferred embodiment, the medication is an anesthetic which is administered prior to removal of the medical tube from the patient's body so as to provide an analgesic effect and reduce pain and discomfort associated with the tube removal.

All patents, patent applications, provisional applications, and publications referred to or cited herein are incorporated by reference in their entirety to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims.

References

U.S. Pat. No. 5,389,074
U.S. Pat. No. 5,279,594
U.S. Pat. No. 5,417,671
U.S. Pat. No. 5,279,552
U.S. Pat. No. 4,717,385

Valenzuela, Roberto C., David A. Rosen (1999) "Topical Lidocaine-Prilocaine Cream (EMLA) for Thoracostomy Tube Removal" *Anesth Anal* 88:1107–1108.

What is claimed is:

1. A collar device for providing a drug or medication to an area of a body of an animal or human where a tube or medical device enters said body, said collar device comprising a collar adapted to fit around said tube or medical device, said collar comprising:

a) a cylinder wall having an inner surface and an outer surface, said outer surface being in contact with said area of said body where said tube or medical device enters said body, b) a slit along the axial length of said cylinder wall forming a first and second edge, wherein said first and second edge comprise a means for interlocking said first and second edge together to secure said collar device around said tube or medical device; and c) means for delivery of said drug or medication to said area of said body where said tube or medical device enters said body, wherein said means for delivery comprises open channels on said outer surface of said cylinder wall, said channels being in open communication with said area of said body where said tube or medical device enters said body.

2. The collar device of claim 1, wherein said inner surface of said cylinder wall comprises an adhesive for securing said collar device around said tube or medical device.

3. The collar device of claim 1, wherein said inner surface of said cylinder wall comprises a medication delivery port.

4. The collar device of claim 3, wherein said medication delivery port is adapted to be inserted into or fit within a groove located on said tube or medical device.

5. A method for delivering a drug or medication to an area of a body of an animal or human where a tube or device enters said body, said method comprising:

a) inserting said tube or medical device having a collar device attached to said tube or medical device, wherein said collar device comprises:
   i) a cylinder wall having an inner surface and an outer surface, said outer surface being in contact with said area of said body where said tube or medical device enters said body;
   ii) a slit along the axial length of said cylinder wall forming a first and second edge, wherein said first and second edge comprise a means for interlocking said first and second edge together to secure said collar device around said tube or medical device; and
   iii) means for delivery of said drug or medication to said area of said body where said tube or medical device enters said body, wherein said means for delivery comprises open channels on said outer surface of said cylinder wall, said channels being in open communication with said area of said body where said tube or medical device enters said body;

b) positioning said attached collar device at said entry site and in contact with tissue of said body at said entry site; and c) delivering said drug or medication to said collar device, wherein said drug or medication passes through said collar device and is, delivered to said tissue.

6. The method according to claim 5, wherein said drug or medication is an anesthetic.

7. The method according to claim 6, wherein said anesthetic is selected from the group consisting of lidocaine, prilocaine and dibucaine.

8. The method according to claim 6, wherein the anesthetic is delivered to said collar device prior to removal of said tube or medical device from said body.

9. A collar device for providing a drug or medication to an area of a body of an animal or human where a tube or medical device enters said body, said collar device comprising a collar adapted to fit around said tube, said collar comprising:

a) a cylinder wall having an inner surface and an outer surface, said outer surface being in contact with said area of said body where said tube or medical device enters said body, b) a slit along the axial length of said cylinder wall forming a first and second edge, wherein said first and second edge comprise a means for interlocking said first and second edge together to secure said collar device around said tube or medical device, and c) means for delivery of said drug or medication to said area of said body where said tube or medical device enters said body, wherein said means for deliver comprises channels in said cylinder wall, said channels being in fluid communication with said outer surface through openings in said cylinder wall from the outer surface through to said channels.

10. The collar device of claim 9, wherein said inner surface of said cylinder wall comprises medication delivery port.

11. The collar device of claim 9, wherein said drug or medication is an anesthetic.

12. The collar device of claim 11, wherein said anesthetic is selected from the group consisting of lidocaine, prilocaine and dibucaine.

13. The collar device of claim 9, wherein said inner surface of said cylinder wall comprises an adhesive for securing said collar device around said tube or medical device.

14. The collar device of claim 10, wherein said medication delivery port is adapted to be inserted into or fit within a groove located on said tube or medical device.

15. A method for delivering a drug or medication to an area of a body of an animal or human where a tube or device enters said body, said method comprising:

a) inserting said tube or medical device having a collar device attached to said tube or medical device, wherein said collar device comprises:
   i) a cylinder wall having an inner surface and an outer surface, said outer surface being in contact with said area of said body where said tube or medical device enters said body;
   ii) a slit along the axial length of said cylinder wall forming a first and second edge, wherein said first and second edge comprise a means for interlocking said first and second edge together to secure said collar device around said tube or medical device; and
   iii) means for delivery of said drug or medication to said area of said body where said tube or medical device enters said body, wherein said means for delivery comprises channels in said cylinder wall, said channels being in fluid communication with said outer surface through openings in said cylinder wall from the outer surface through to said channels;

b) positioning said attached collar device at said entry site and in contact with tissue of said body at said entry site; and c) delivering said drug or medication to said collar device, wherein said drug or medication passes through said collar device and is delivered to said tissue.

16. The method according to claim 15, wherein said drug or medication is an anesthetic.

17. The method according to claim 16, wherein said anesthetic is selected from the group consisting of lidocaine, prilocaine and dibucaine.

18. The method according to claim 16, wherein the anesthetic is delivered to said collar device prior to removal of said tube or medical device from said body.

* * * * *

UNITED STATES PATENT AND TRADEMARK OFFICE
CERTIFICATE OF CORRECTION

PATENT NO. : 6,402,735 B1
DATED : June 11, 2002
INVENTOR(S) : Paul B. Langevin

It is certified that error appears in the above-identified patent and that said Letters Patent is hereby corrected as shown below:

Column 6,
Line 6, "for deliver" should read -- for delivery --.

Signed and Sealed this

Eleventh Day of February, 2003

JAMES E. ROGAN
*Director of the United States Patent and Trademark Office*